Figure 1:
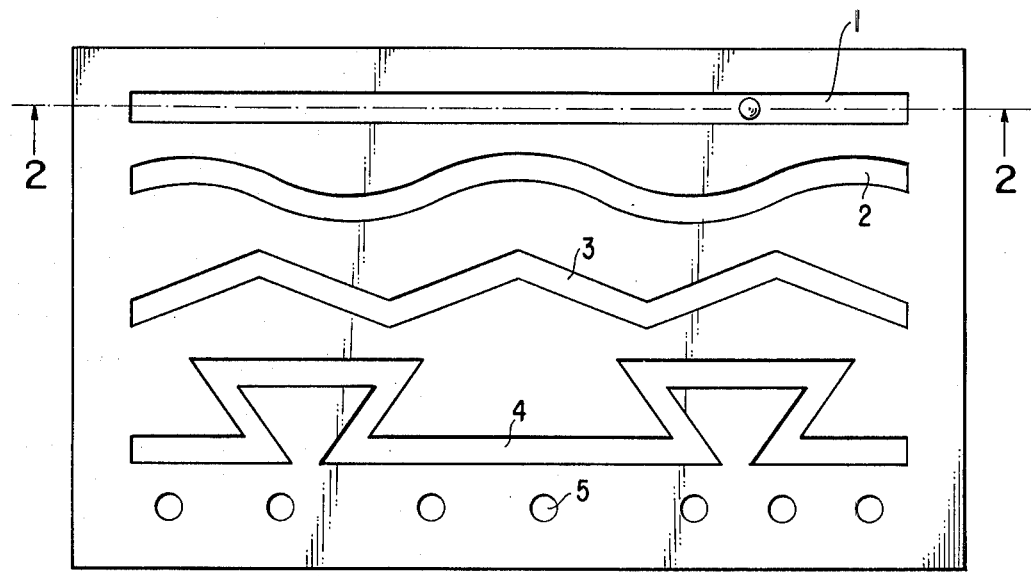

United States Patent [19]

Krass

[11] 4,276,546
[45] Jun. 30, 1981

[54] MOTOR SKILLS TESTER

[76] Inventor: Alvin Krass, 205 Holland Rd., Holmdel, N.J. 07733

[21] Appl. No.: 156,935

[22] Filed: Jun. 6, 1980

[51] Int. Cl.³ .......................................... G08B 21/00
[52] U.S. Cl. .................................. 340/576; 340/52 R
[58] Field of Search ........................ 340/52 R, 53, 576

[56] References Cited

U.S. PATENT DOCUMENTS 3,755,776  8/1973  Kotras .................................. 340/576
3,794,968  2/1974  Hill ....................................... 340/576

Primary Examiner—Alvin H. Waring
Attorney, Agent, or Firm—Harry E. Westlake, Jr.

[57] ABSTRACT

An apparatus and method for testing impairment of motor skills is described comprising an electrically conducting stylus to be passed by the person being tested down a series of slots in a planar solid, the slots being in a variety of geometric shapes and having an electrically conducting edge, the stylus and the slot edges being connected to timing and counting means.

7 Claims, 2 Drawing Figures

U.S. Patent    Jun. 30, 1981    4,276,546

MOTOR SKILLS TESTER

This invention relates to a method of determining the extent to which motor skills have been affected by brain or central nervous system impairment and to an electrical device for effecting such determination.

More specifically, it relates to a method of testing motor skills retained by persons with impaired brain function which comprises having the person pass a hand held electrically conducting stylus down each of a series of slots in a planar solid, said slots having a variety of geometric shapes but always having a width only slightly bigger than the stylus, each of the slots having electric contacts at each end connected to a timing means and electrical conducting edging connected through an alarming means and a counting means to said stylus. More specifically also it relates to the device used to carry out the method.

BACKGROUND OF THE INVENTION

One of the first results of brain or central nervous system impairment is a reduction of motor skills, that is, the ability to control the motion of limbs, especially the hand, with any accuracy. One of the first controls to be lost is that over change in direction in moving the hands. Still many persons suffering from brain impairment can be trained, if the extend to which they retain motor skills can be determined, to perform many useful functions in life. Thus, an accurate means for evaluating such skills is an important tool too for the rehabilitation of such people and the finding for them of a useful place in society.

Past methods of testing motor skills have varied. One such involved testing their ability to perform specific mechanical tasks. Another involved testing their accuracy in the use of writing devices to draw accurately or to make lines within designated pathways on paper. In either case the speed and accuracy of the performance was a vital part of the test. Determining speed and accuracy was not always easily done. A more accurate and faster method of determining both simultaneously was needed.

THE PRESENT INVENTION

I have found that the testing of motor skills can be carried out easily, speedily and accurately by having the person being tested pass an electrically conducting stylus down one or more narrow slots just a little wider than the stylus and having an electrically conducting edging connected electrically to the stylus through counting and alarming devices, while an electrically activated timing device, activated at the ends of the slots by the stylus, simultaneously measures the time of the passage. The person is instructed to pass the stylus down the full length of each slot without contacting the edge. The number of such contacts indicates the impairment of motor skills. The slots have shapes of increasing geometrical complexity as well as varying widths such that successive trials become more difficult and exacting. Thus, an estimate of motor skill impairment can be obtained from the speed, accuracy and care which the person exhibits in each. These in turn can be related to the potential of the persons to perform specific occupations.

Figure 2:
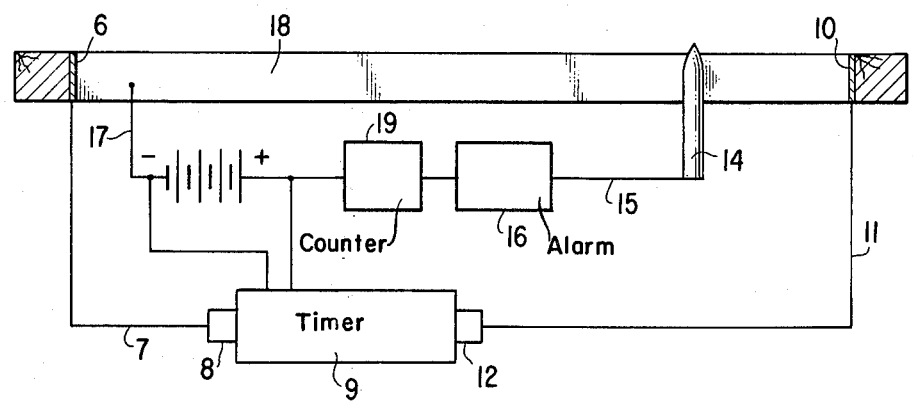

The apparatus used in this invention, which itself forms one aspect of this invention, can be further illustrated with reference to the drawings in which FIG. 1 is a plan view of the planar solid showing a number of slots of differing shapes, and FIG. 2 is a sectional view through the line 2—2 showing also, schematically, an electrical operating circuit.

In FIG. 1, the slot paths increase in complexity from a straight line 1 through curves 2, zig-zags 3 and acute angles 4 to a series of round holes 5. Depending on how accurately and extensively the motor skills are to be measured, the shapes and complexity of the slots geometry can be varied at will.

In FIG. 2, a section down the straight line slot 1 is shown connected to the necessary operating electrical devices. At each end of the slot 1 are electrical contacts 6 and 10. Contact 6 is connected by wire 7 to the starting mechanism 8 of a time device 9 (both shown schematically). Contact 10 is connected by wire 11 to the stopping mechanism 12. The timing device 9 is powered by a battery 13. An electrically conducting stylus 14 is connected by wire 15 through an alarming device 16 (shown schematically) to one pole of battery 13 while the other pole of the battery is connected electrically by wire 17 to the electrically conducting edge 18 of the slot 1. An electrically activated counting means 19 is also placed in the stylus circuit.

Variations can be made in the above described structure. The electric source need not be a battery 13 but can be an alternating current source such as an ordinary 110 volt house socket. The alarming means 16 may be a buzzer, a bell or an electric light to provide either audible or visual alarms, or both kinds can be used. If desired, they can be eliminated entirely. The counting device 19 can be any convenient electrically activated device which will record and/or display the number of contacts made during the passage. Conveniently it is a digital display device which can be reset after each slot passage. Any timing device which can be electrically initiated and stopped can be used.

The stylus 14 can be of any shape desired provided it fits into the slot with more or less room to spare. The closer the fit, the more delicate will be the control necessary for a perfect passage. It can also be cordless, connected to the rest of the circuit by radio waves.

The circuiting shown in FIG. 2 is repeated for each slot of more complex geometry. Normally only one stylus 14, one alarming system 16, one counter 19 and one timer 9 are used, all being connected simultaneously in the same way to each slot or hole.

In carrying out the testing by the method of this invention, using the device of this invention, the person being tested takes the stylus in hand and touches the starting contact 6. He is then required to pass the stylus down the slot as fast and as accurately as he can and touch the stopping contact 10. The number of contacts made and the passage time are recorded. The person then repeats the test in the next more difficult slot. A table of timing and accuracy is then constructed for the individual. Through experience with a large number of individuals, I have found it possible to correlate the numbers so obtained with the potential ability to carry out various economic occupational tasks.

It is an advantage of this invention that the testing uses a progressive increase in task difficulty and can be varied as desired to provide measurements of skills requiring a wide gamut of control. It is a further advantage that the results can be accurately and swiftly obtained in the form of a number score which can then be related to a rating of motor control ability and eventually to the ability to perform designated useful tasks.

This invention thus is a very valuable tool in the assessment of the extent of impairment of handicapped people and a guide to their rehabilitation into society.

I claim:

1. A method of testing the motor skills retained by persons with impaired brain function which comprises having said person pass a hand held electrically conducting stylus down the length of each of a series of slots in a planar solid, said slots having a variety of geometric shapes of increasing complexity, but having a width not much bigger than said stylus, each of said slots further having electric contacts at each end connected to an electrically activated timing means, said slots also having an electrically conducting edging connected to means for effecting an alarm at each contact of the stylus with said edging and to means for recording the number of said contacts in the passage down each slot.

2. The method of claim 1 in which said alarm means is an electrically activated noise producing device.

3. The method of claim 1 in which said alarm means is an electric lamp.

4. The method of claim 1 in which said alarm means includes both an electrically activated noise producing device and an electric lamp.

5. A device for testing the motor skills of a person with impaired brain function which comprises, in combination
    (a) a planar solid having plurality of slots cut out thereof;
    (b) said slots being shaped in a variety of widths and geometric shapes of differing complexity varying from straight lines to curves, angles and circles;
    (c) said slots having electric contacts at either end connected to the start and stop mechanism of a timing means;
    (d) said slots having all the edges lined with an electrically conducting material connected to at least one means for effecting an alarm and with an electrically activated counting means; and
    (e) a hand held electrically conducting stylus connected electrically to said alarm means such that each contact with said electrically conducting slot lining activates said alarm and said counting means.

6. The device of claim 5 in which the alarming means is an electric lamp.

7. The device of claim 5 in which the alarming means is an electrically activated noise producing device.

* * * * *